US012575964B2

(12) United States Patent
Lee et al.

(10) Patent No.: US 12,575,964 B2
(45) Date of Patent: Mar. 17, 2026

(54) COLD AND HOT PACK FOR BREAST THERAPY FOR PREGNANT WOMAN

(71) Applicant: TENBOX CORP., Seongnam-si (KR)

(72) Inventors: Eun Ki Lee, Seongnam-si (KR); Jin Ju Baek, Seongnam-si (KR); Ji Woo Shin, Yongin-si (KR)

(73) Assignee: TENBOX CORP., Seongnam-si Gyeonggi-do (KR)

( * ) Notice: Subject to any disclaimer, the term of this patent is extended or adjusted under 35 U.S.C. 154(b) by 399 days.

(21) Appl. No.: 18/023,267

(22) PCT Filed: Sep. 14, 2020

(86) PCT No.: PCT/KR2020/012371
§ 371 (c)(1),
(2) Date: Feb. 24, 2023

(87) PCT Pub. No.: WO2022/054998
PCT Pub. Date: Mar. 17, 2022

(65) Prior Publication Data
US 2023/0293341 A1 Sep. 21, 2023

(30) Foreign Application Priority Data
Sep. 8, 2020 (KR) ........................ 10-2020-0114948

(51) Int. Cl.
*A61F 7/02* (2006.01)
*A61F 7/00* (2006.01)
(52) U.S. Cl.
CPC ........ *A61F 7/02* (2013.01); *A61F 2007/0021* (2013.01); *A61F 2007/022* (2013.01);
(Continued)

(58) Field of Classification Search
CPC ................ A61F 7/02; A61F 2007/0021; A61F 2007/022; A61F 2007/0228; A61F 2007/0231
See application file for complete search history.

(56) References Cited

U.S. PATENT DOCUMENTS

| | | | | |
|---|---|---|---|---|
| 5,111,810 A | * | 5/1992 | Fortney ..................... | A61F 7/02 607/108 |
| 5,679,052 A | * | 10/1997 | Rucki ....................... | A61F 7/02 450/38 |

(Continued)

FOREIGN PATENT DOCUMENTS

| | | |
|---|---|---|
| CN | 210784874 U | 6/2020 |
| JP | 2019-000533 A | 1/2019 |

(Continued)

*Primary Examiner* — Joseph A Stoklosa
(74) *Attorney, Agent, or Firm* — Bridgeway IP Law Group, PLLC; Jihun Kim

(57) ABSTRACT

A hot and cold pack for breast treatment for pregnant women is provided. The hot and cold pack for breast treatment for pregnant women includes a cover including a through hole in a center thereof, through which a user's nipple passes, and having an annular shape of which a portion is open to adjust a size according to the size of a user's breast while wrapping and covering the user's breast, a thermal insulating material filled inside the cover, and a length adjustment unit provided in the open portion of the cover to connect both sides of the open cover, and adjusting the size of the cover.

8 Claims, 8 Drawing Sheets

(52) U.S. Cl.
        CPC ................ *A61F 2007/0228* (2013.01); *A61F 2007/0231* (2013.01)

(56)                     References Cited

U.S. PATENT DOCUMENTS

| | | | | |
|---|---|---|---|---|
| 6,042,604 | A | * | 3/2000 | Gennetti ................ A61G 7/065 5/636 |
| 6,241,715 | B1 | * | 6/2001 | Houser ................ A61F 13/141 604/385.07 |
| 2005/0070980 | A1 | * | 3/2005 | Noonan .................... A61F 7/02 607/108 |
| 2011/0015708 | A1 | * | 1/2011 | Lee ...................... A61F 5/0193 128/121.1 |
| 2014/0188199 | A1 | * | 7/2014 | Enderby .............. A61M 1/062 607/108 |
| 2018/0078424 | A1 | * | 3/2018 | Galazin, Jr. .............. A61F 7/03 |
| 2019/0099289 | A1 | * | 4/2019 | Beck ...................... A61J 13/00 |
| 2019/0269548 | A1 | * | 9/2019 | Fan ......................... C08L 33/02 |
| 2020/0268550 | A1 | * | 8/2020 | Mehta ..................... A61F 7/02 |
| 2021/0060288 | A1 | * | 3/2021 | Julius .................... A61H 7/007 |

FOREIGN PATENT DOCUMENTS

| | | | | | |
|---|---|---|---|---|---|
| KR | 10-2004-0019830 | A | | 3/2004 | |
| KR | 20040019830 | A | * | 3/2004 | .............. A61F 7/02 |
| KR | 20-0357255 | Y1 | | 7/2004 | |
| KR | 10-2020-0040394 | A | | 4/2020 | |

* cited by examiner

COLD AND HOT PACK FOR BREAST THERAPY FOR PREGNANT WOMAN

TECHNICAL FIELD

The present disclosure relates to a hot and cold fomentation pack for breast treatment for pregnant women. More specifically, the present disclosure relates to a hot and cold fomentation pack for pregnant women' breast treatment that may be adjusted in size and shape to suit the shape of a user's breast and is capable of performing a breast massage.

BACKGROUND ART

Women need breast massage for some reasons such as breast lumps, mastitis, a milk fever, and an increase in the amount of breast milk at each time, such as pregnancy and childbirth. Men are also increasingly using breast fomentation for reasons such as relieving muscle pain following strenuous exercise. However, generally, in most cases, a cloth such as a towel is soaked in hot water and used for breast fomentation, or a cloth is wrapped around ice cubes to perform heat or cold fomentation.

In this case, uniform fomentation is difficult to achieve depending on the shape of the cloth. To address this problem, breast fomentation packs are being sold, but it is difficult to change the sizes and shapes of these breast fomentation packs. Thus, it is difficult to apply uniform fomentation to various shapes of breasts.

DESCRIPTION OF EMBODIMENTS

Technical Problem

Provided is a hot and cold pack for pregnant women' breast treatment, of which the size and shape may be modified according to various breast sizes and shapes.

Provided is a hot and cold pack for pregnant women' breast treatment that may maintain a changed shape by using a fixing device.

Provided is a hot and cold pack for pregnant women' breast treatment that may enable uniform fomentation on a breast part by preventing a thermal insulating material from tilting according to fomentation postures.

Provided is a hot and cold pack for pregnant women' breast treatment that may prevent skin troubles by smoothly absorbing the sweat generated during hot fomentation.

The technical problems of the present disclosure are not limited to the above-mentioned contents, and other technical problems not mentioned will be clearly understood by a person skilled in the art from the following description.

Technical Solution

According to an embodiment of the present disclosure, a hot and cold pack for pregnant women' breast treatment includes a cover including a through hole in a center thereof, through which a user's nipple passes, and having an annular shape of which a portion is open to adjust a size according to the size of a user's breast while wrapping and covering the user's breast, a thermal insulating material filled inside the cover, and a length adjustment unit provided in the open portion of the cover to connect both sides of the open cover, and adjusting the size of the cover, wherein the cover includes a folding guide unit for guiding the cover to be curved and folded into a suitable shape according to the shape of the breast.

The length adjustment unit may include a strap provided on one side of the open portion of the cover and having a predetermined length, and a fastener provided on the other side of the open portion of the cover and including a slit to which the strap is fastened. The strap may be inserted into an insertion hole between the fastener and the cover and then reinserted into the slit and fixed.

The length adjustment unit may be a Velcro including a hook provided on one side of the open portion of the cover and a loop provided on the other side of the open portion of the cover.

The length adjustment unit may include an embossed button provided on one side of the open portion of the cover and an engraved button provided on the other side of the open portion of the cover and coupled with the embossed button. The engraved button may be provided in plurality along a circumferential direction of the cover, and the size of the cover may be adjusted according to a position of engagement with the embossed button.

The length adjustment unit may include a strap provided on one side of the open portion of the cover and having a predetermined length, a guide portion provided on one end of the strap, and a sliding portion provided on the other side of the open portion of the cover and to which the guide portion is coupled to guide a linear movement. As the guide portion moves on the sliding portion, the size of the cover may be adjusted.

The through hole may be cut at regular intervals in a circumferential direction of the through hole so as to easily bend the cover.

The cover may include an upper cover and a lower cover each having an annular shape with an open portion and being bonded to each other.

The hot and cold pack for pregnant women' breast treatment may include a plurality of radial junction portions bonding the upper cover with the lower cover and being spaced apart from each other at predetermined intervals, in a radial direction with respect to the through hole, so as to prevent tilting of the thermal insulating material within the cover.

The hot and cold pack for pregnant women' breast treatment may include a plurality of circumferential junction portions bonding the upper cover with the lower cover and being spaced apart from each other at predetermined intervals, in a circumferential direction with respect to the through hole, so as to prevent tilting of the thermal insulating material within the cover.

The hot and cold pack for pregnant women' breast treatment may further include an outer covering made of a sweat absorbing material to absorb the user's sweat and formed to correspond to the shape of the cover so as to surround the cover. The outer covering may include one or more openings so that the length adjustment unit is usable while the outer covering wraps the cover.

The hot and cold pack for pregnant women' breast treatment may further include a nipple protection unit fitted along a circumference of the through hole to protect the nipple.

Effects of Disclosure

A hot and cold pack for breast treatment for pregnant women according to an embodiment of the present disclosure may be modified in size and shape according to various breast sizes and shapes.

The hot and cold pack for breast treatment for pregnant women according to an embodiment of the present disclosure may maintain a deformed shape by using a fixing device.

The hot and cold pack for breast treatment for pregnant women according to an embodiment of the present disclosure may prevent a thermal insulating material from tilting according to fomentation postures.

The hot and cold pack for pregnant women' breast treatment according to an embodiment of the present disclosure may prevent skin troubles by smoothly absorbing the sweat generated during hot fomentation.

The effects of the present disclosure are not limited to the above-mentioned contents, and other effects not mentioned will be clearly understood by a person skilled in the art from the following description.

BEST MODE

Figure 1:
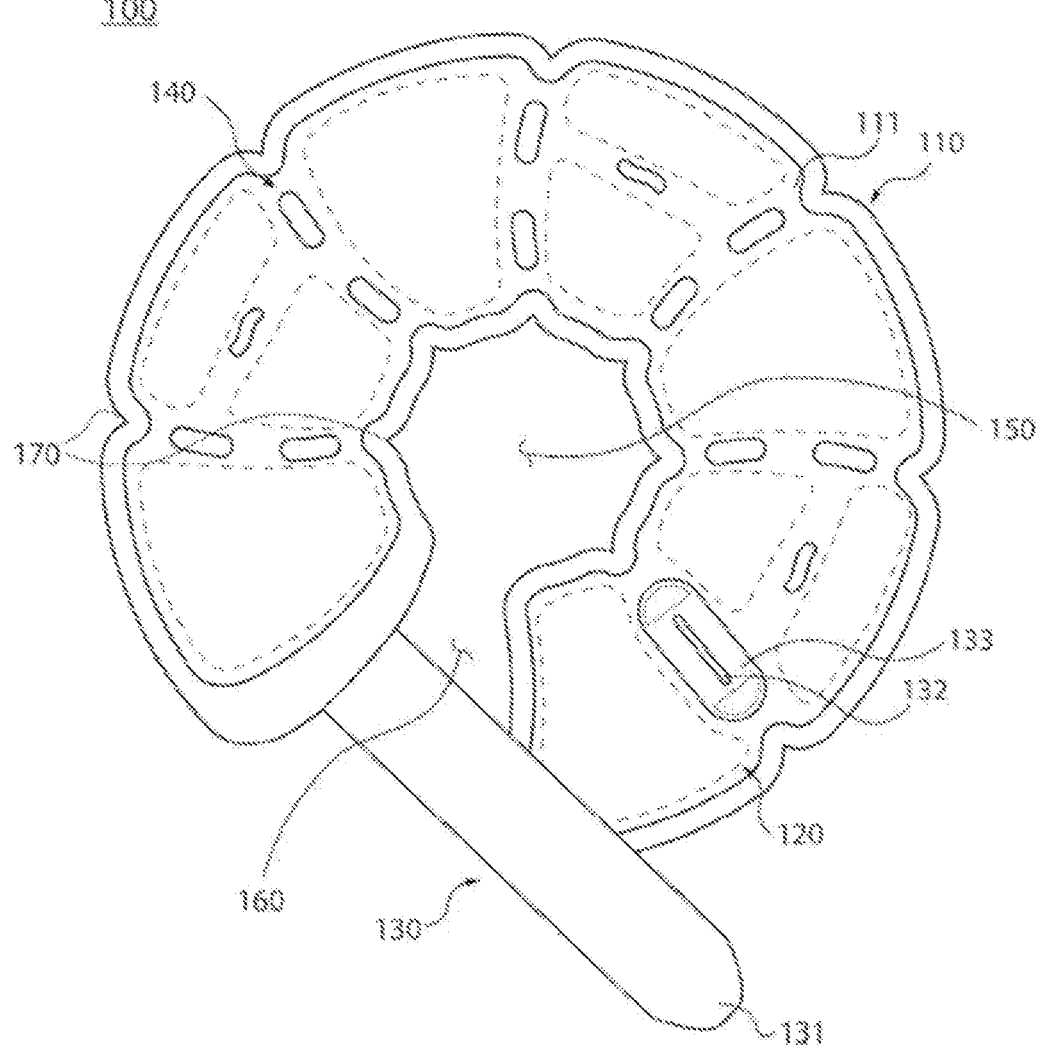
FIG. 1 is a plan view of a hot and cold pack for pregnant women' breast treatment according to a first embodiment of the present disclosure.

Embodiments of the present disclosure will now be described more fully with reference to the accompanying drawings such that one of ordinary skill in the art to which the present disclosure pertains may easily execute the present disclosure. The present disclosure may, however, be embodied in many different forms and should not be construed as being limited to the embodiments set forth herein.

In the drawings, elements irrelevant to the descriptions of the present disclosure are omitted to clearly explain the present disclosure.

The terms used in the present specification are merely used to describe particular embodiments, and are not intended to limit the present disclosure. An expression used in the singular may encompass the expression of the plural, unless it has a clearly different meaning in the context.

In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

In addition, the components shown in the embodiments of the present disclosure are shown independently to indicate different characteristic functions, and do not mean that each component is separate hardware or one software component. In other words, for convenience of description, each component is listed and described as each component, and at least two components of each component may be combined to form one component, or one component may be divided into a plurality of components to perform a function. The integrated and separate embodiments of each component are also included in the scope of the present disclosure without departing from the essence of the present disclosure.

In addition, the following embodiments are provided to more clearly explain to one of ordinary skill in the art, and the shapes and sizes of elements in the drawings may be exaggerated for clearer explanation.

Hereinafter, embodiments of the present disclosure will be described more fully with reference to the accompanying drawings.

Figure 2:
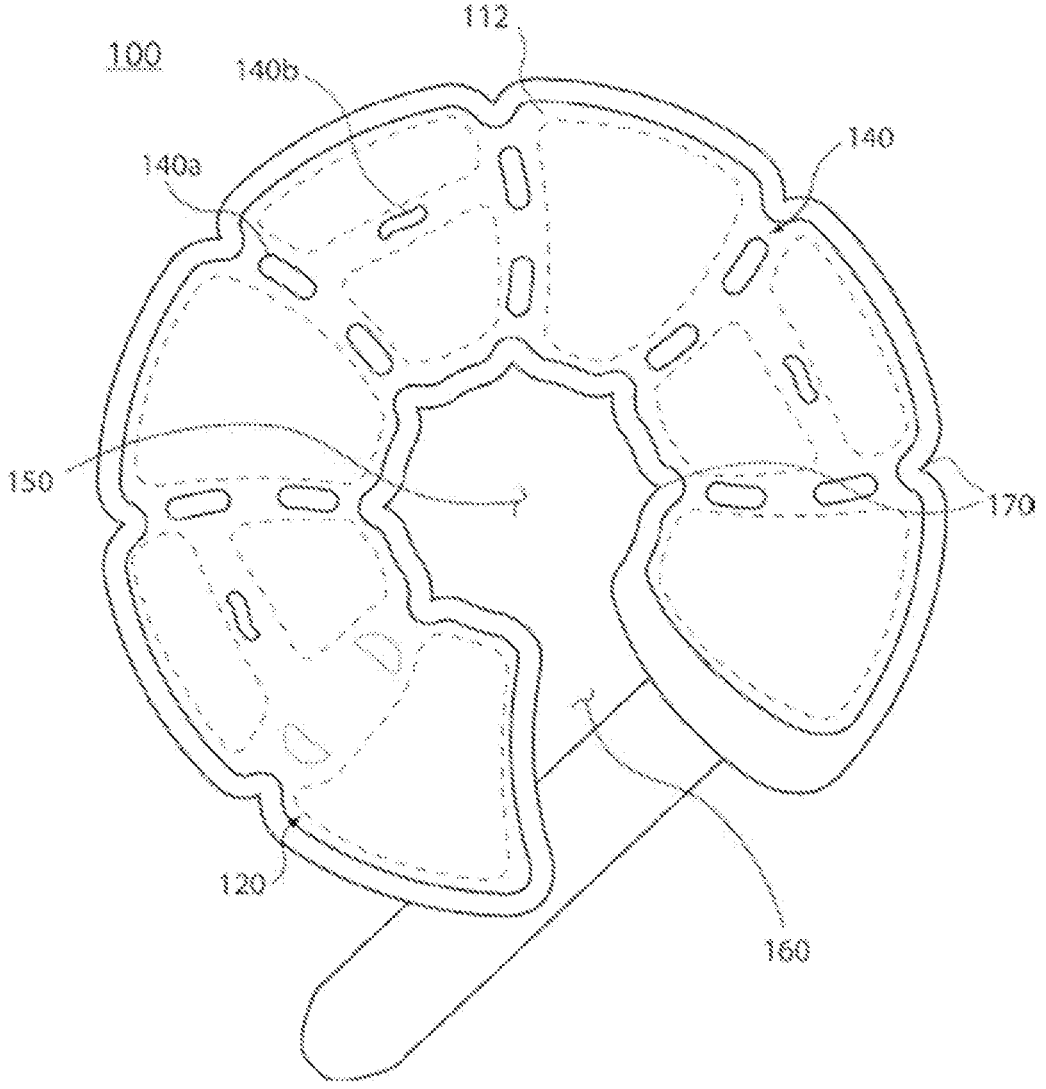
FIG. 2 is a bottom view of the hot and cold pack for pregnant women' breast treatment according to the first embodiment of the present disclosure.

FIG. 1 is a plan view of a hot and cold pack for pregnant women' breast treatment according to a first embodiment of the present disclosure, and FIG. 2 is a bottom view of the hot and cold pack for pregnant women' breast treatment according to the first embodiment of the present disclosure.

Referring to FIGS. 1 and 2, a hot and cold pack 100 for breast treatment for pregnant women according to a first embodiment of the present disclosure is provided for hot or cold fomentation on the breast, and may include a cover 110, a thermal insulating material 120, a length adjustment unit 130, and a folding guide unit 140.

The cover 110 may be formed by bonding an upper cover 111 and a lower cover 112 together each having an annular shape, and may be partially opened to adjust its size according to the size of a user's breast.

The cover 110 is a portion that directly contacts the user's breast, and may have an annular shape with a through hole 150 through which the user's nipple passes at its center so as to surround and cover the user's breast. The user may use the hot and cold pack 100 by rounding the cover 110 about the through hole 150 to deform the cover 110 to fit the shape of the breast, then passing his or her nipple through the through hole 150, and placing the lower cover 112 on the breast.

The cover 110 and the through hole 150 have cutout portions 170 cut at regular intervals in an outer circumferential direction of the cover 110 and a circumferential direction of the through hole 150 such that the cover 110 may be easily bent.

Because the cover 110 is in direct contact with the user's skin, the cover 110 may be formed of a non-toxic PVC material or a silicon material. The inside of the cover 110 may be filled with the thermal insulating material 120. The thermal insulating material 120 is provided to maintain the temperature of the hot and cold pack 100 for breast treatment for pregnant women. According to the present embodiment, the thermal insulating material 120 may be in the form of a gel, but there are no restrictions on its material and its shape.

The length adjustment unit 130 is provided to adjust the size of the cover 110 and fix the shape of the cover 110. The length adjustment unit 130 is provided on an open portion 160 of the cover 110 to connect both sides of the open cover 110 and adjust the size of the cover 110.

The folding guide unit 140 is provided to be deformed according to the size of the user's breast on which the hot and cold pack 100 is to be applied, and may guide the cover 110 such that the cover 110 is easily bent and folded. According to the present embodiment, the folding guide unit 140 may be formed by bonding the upper cover 111 with the lower cover 112.

The hot and cold pack 100 for breast treatment for pregnant women according to the present embodiment may include a plurality of junctions 140. The junctions 140 has the same configuration as the folding guide unit 140. Hereinafter, the folding guide unit 140 will be described as the junctions 140.

The junctions 140 are a portion that separates the inner space of the cover 110 by bonding the upper cover 111 with the lower cover 112, and is provided to prevent the thermal insulating material 120 from being tilted. The junctions 140 may include a radial junction portion 140a for preventing horizontal tilting of the thermal insulating material 120 and a circumferential junction 140b for preventing vertical tilting of the thermal insulating material 120. The radial junction 140a may be formed by bonding the upper cover 111 and the lower cover 112 together at regular intervals in the radial direction with respect to the through hole 150, and the circumferential junction 140b may be formed by bonding the upper cover 111 and the lower cover 112 together at regular intervals in the circumferential direction with respect to through the through hole 150.

The junctions 140 may prevent the thermal insulating material 120 from tilting according to the user's fomentation posture, so that fomentation on the user's breast may be uniformly performed. The circumferential junction 140b may prevent the thermal insulating material 120 around the through hole 150 from being tilted downwards due to the three-dimensional (3D) shape of the breast, so that fomentation of even a breast portion around the areola may be uniformly performed.

Figure 3:
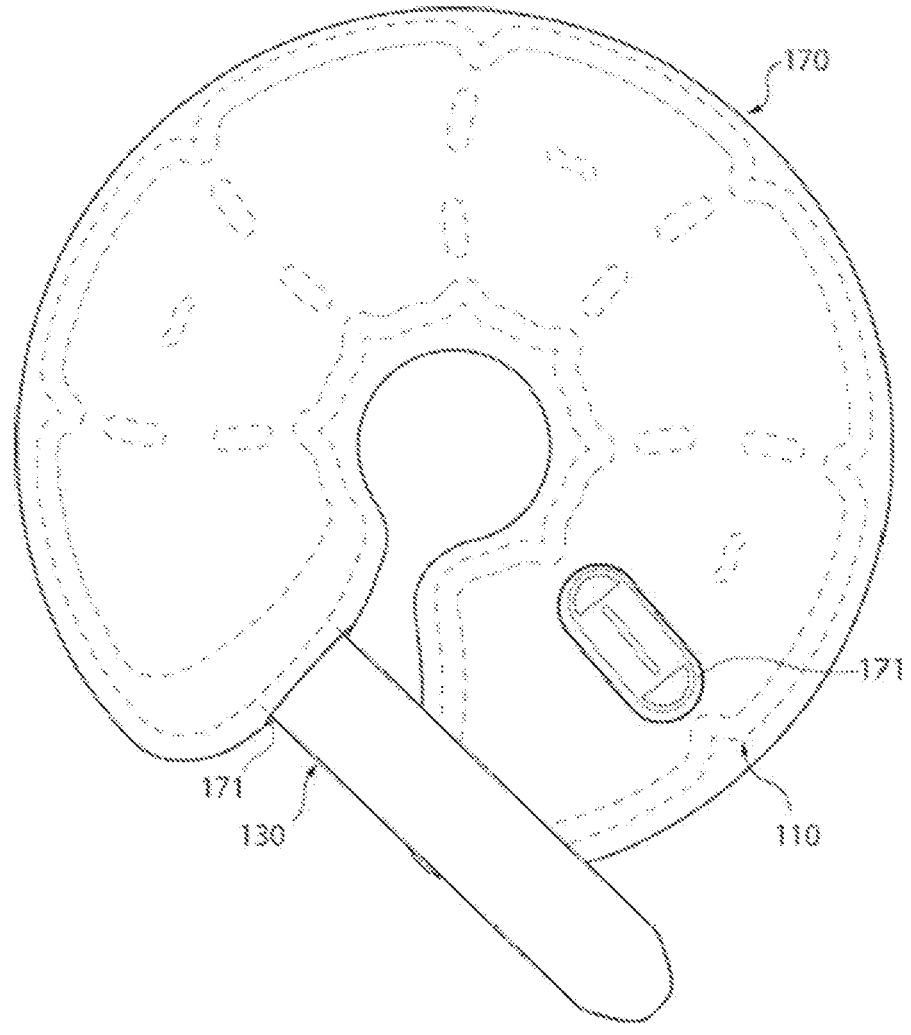
FIG. 3 is a view of an outer covering of the hot and cold pack for pregnant women' breast treatment according to the first embodiment of the present disclosure.

FIG. 3 is a view of an outer covering of the hot and cold pack for pregnant women' breast treatment according to the first embodiment of the present disclosure.

Referring to FIG. 3, the hot and cold pack for pregnant women' breast treatment according to the first embodiment of the present disclosure may further include an outer covering 170.

The outer covering 170 covers the outer surface of the cover 110, and is provided to absorb the user's sweat. Because the material of the cover 110 may be difficult to absorb the user's sweat, an outer covering 170 made of a material capable of absorbing sweat may wrap the cover 110 and may directly contact the user's skin to absorb the user's sweat. The material of the outer covering 170 may be a cotton or cool material that absorbs moisture smoothly.

The outer covering 170 may include one or more openings 171 so that the length adjustment unit 130 may be used while the outer covering 170 is wrapping the cover 110.

Because the outer covering 170 immediately absorbs the sweat generated when the user applies heat to the breast, skin diseases caused by sweat may be prevented.

Figure 4:
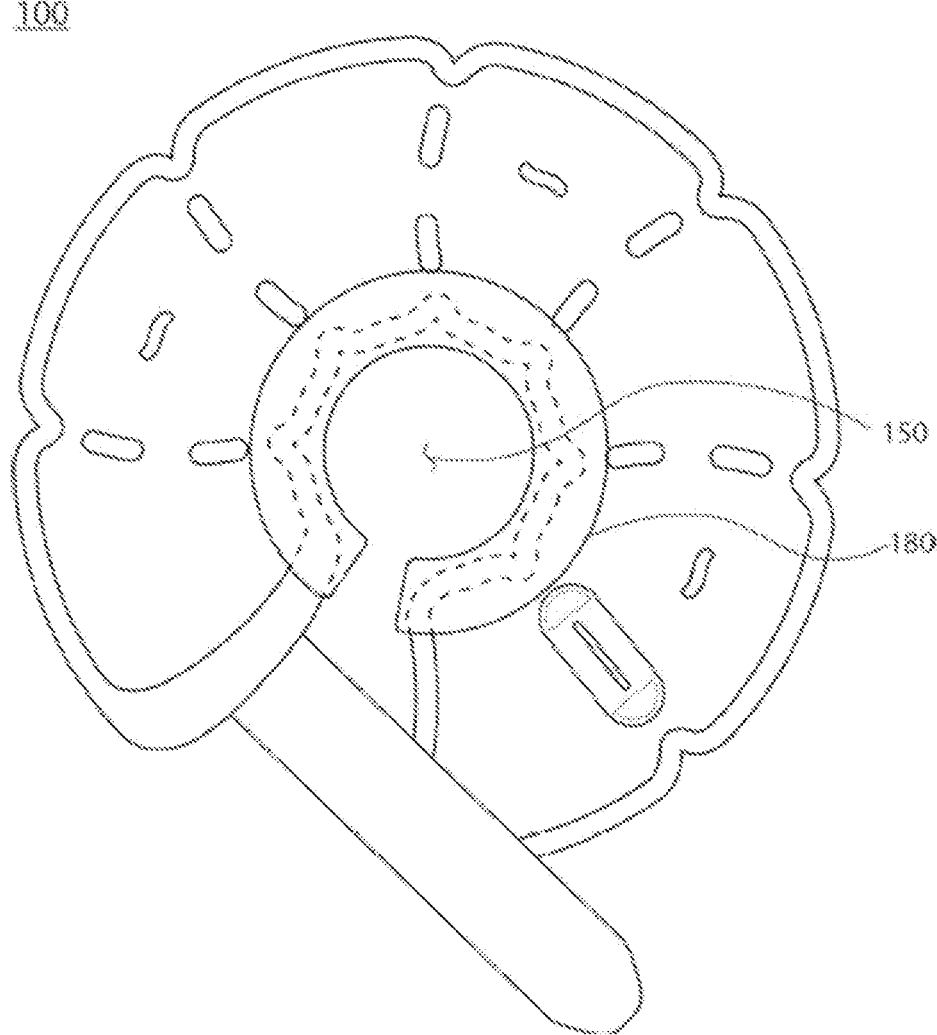
FIG. 4 is a view of a hot and cold pack for pregnant women' breast treatment including a nipple protection unit, according to the first embodiment of the present disclosure.

FIG. 4 is a view of a hot and cold pack for pregnant women' breast treatment including a nipple protection unit, according to the first embodiment of the present disclosure.

Referring to FIG. 4, the hot and cold pack for pregnant women' breast treatment according to the first embodiment of the present disclosure may further include a nipple protection unit 180. The nipple protection unit 180 is provided to protect the user's nipple, and may be inserted along the circumference of the through hole 150.

The circumference of the through hole 150, which is a junction of the upper cover 111 and the lower cover 112 shown in FIGS. 1 and 2, may be sharp, and thus there is a possibility that the nipple is cut during use of the hot and cold pack. The nipple protection unit 180 may protect the nipple by wrapping the circumference of the through hole 150 that may be sharp.

The nipple protection unit 180 may be formed in a shape in which the side of the nipple is curved, and may be formed of, for example, a material such as silicon.

Figure 5A:
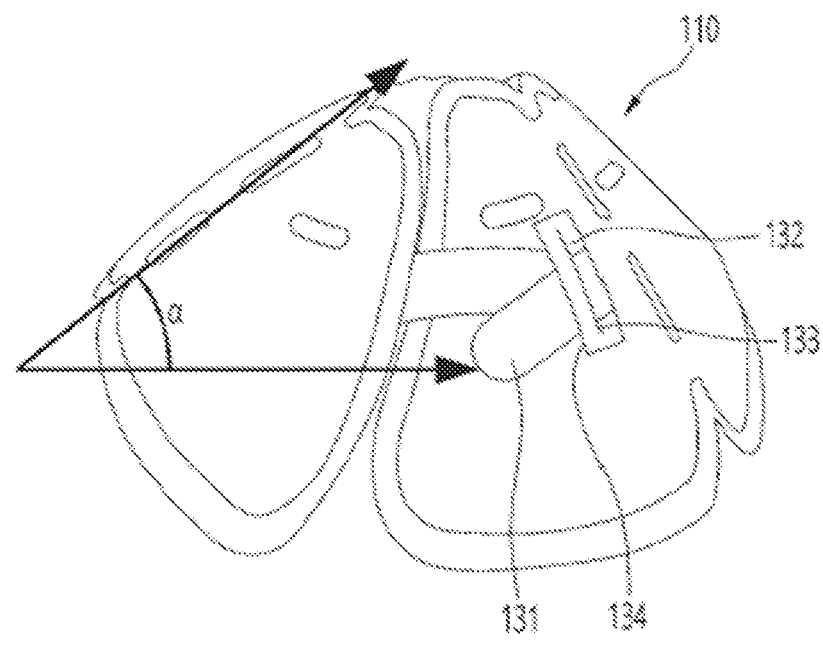
FIGS. 5A and 5B are views illustrating a length adjustment unit according to the first embodiment of the present disclosure and a hot and cold pack for pregnant women' breast treatment in which the length adjustment unit has been fastened.
Figure 5B:
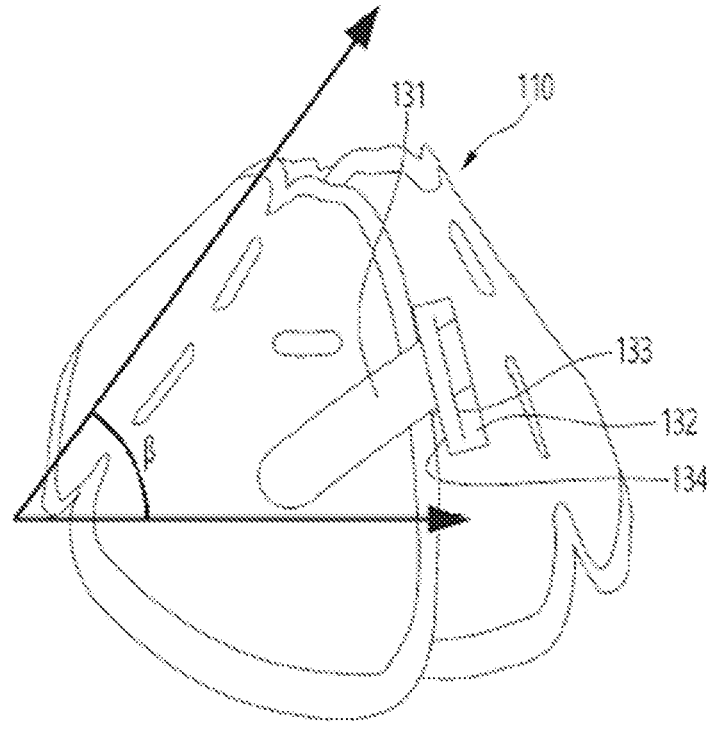

FIGS. 5A and 5B are views illustrating a length adjustment unit according to the first embodiment of the present disclosure and a hot and cold pack for pregnant women' breast treatment in which the length adjustment unit has been fastened.

Referring to FIGS. 5A and 5B, the length adjustment unit 130 according to the first embodiment of the present disclosure may include a strap 131 and a fastener 132.

The length adjustment unit 130 is provided for the user to adjust and fix the size and shape of the cover 110 according to the size and shape of the user's breast.

In detail, the strap 131 may be provided on one side of the open portion 160 of the cover 110 and may have a predetermined length. The fastener 132 may be provided on the other side of the open portion 160 of the cover 110 and have a slit 133 into which the strap 131 is fastened. Both ends of the fastener 132 may be attached to the cover 110, and an insertion hole 134 may be formed between the cover 110 and the fastener 132. The user may adjust the length of the strap 131 so that the cover 110 is adjusted according to the size and shape of the breast, and insert the strap 131 into the insertion hole 134, and may re-insert the strap 131 inserted into the insertion hole 134 into the slit 133, thereby fixing the size and shape of the cover 110.

FIGS. 5A and 5B show the shapes of the cover 110 that are deformed according to the lengths of the strap 131 inserted into the fastener 132. In the hot and cold pack 100 shown in FIG. 5A, the length of the strap 131 inserted into the fastener 132 is small, and thus the shape of the cover 110 may be suitable for a wide breast shape. In the hot and cold pack 100 shown in FIG. 5B, the length of the strap 131 inserted into the fastener 132 is large, and thus the cover 110 is deformed such that an angle between the cover 110 and the ground forms β larger than α, and thus the shape of the cover 110 may be suitable for a protuberant breast shape.

The length adjustment unit 130 according to the present embodiment may freely deform the cover 110 into a shape optimized for the shape of the user's breast and fix the shape.

Mode of Disclosure

Hereinafter, second through fourth embodiments of the present disclosure to be described below are embodiments of a length adjusting unit of a hot and cold pack for breast treatment for pregnant women, and other components are the same as those of the first embodiment.

Figure 6A:
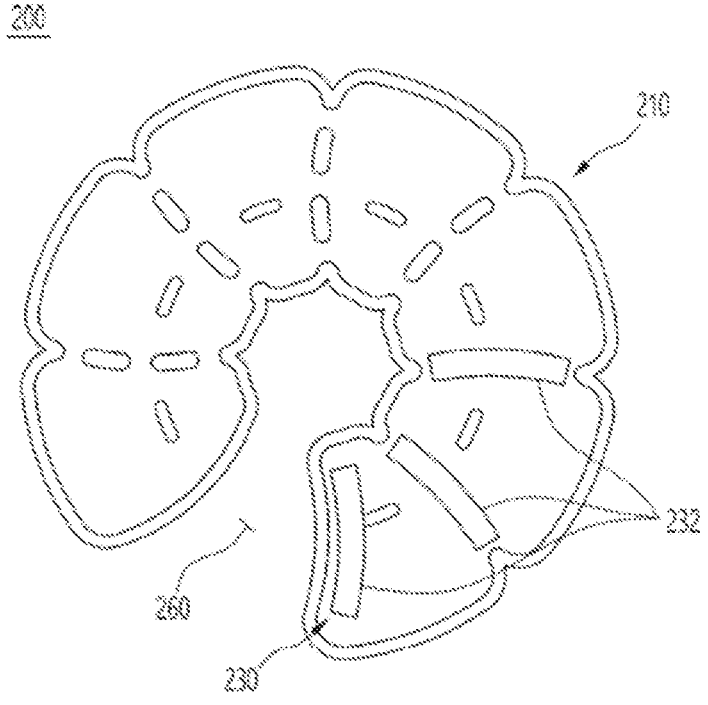
FIG. 6A is a plan view of a hot and cold pack for pregnant women' breast treatment to which a length adjustment unit according to a second embodiment of the present disclosure has been applied.
Figure 6B:
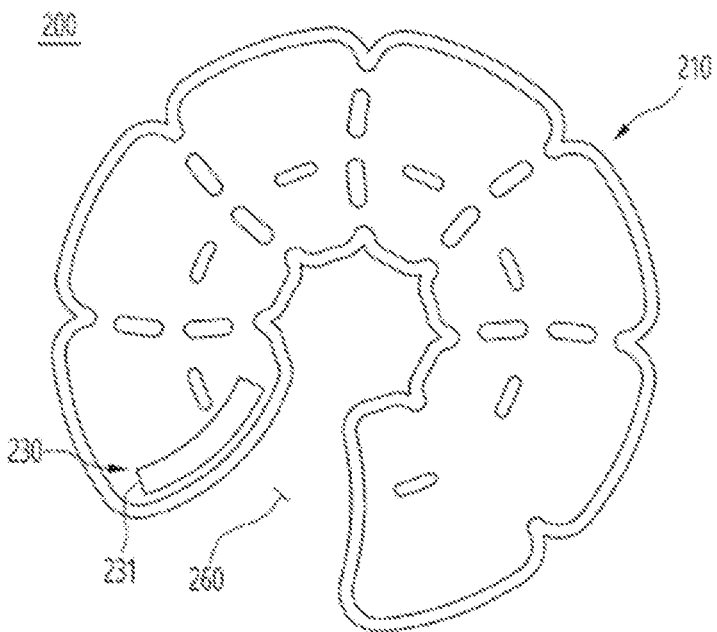
FIG. 6B is a bottom view of the hot and cold pack for pregnant women' breast treatment to which the length adjustment unit according to the second embodiment of the present disclosure has been applied.

FIG. 6A is a plan view of a hot and cold pack for pregnant women' breast treatment to which a length adjustment unit according to a second embodiment of the present disclosure has been applied, and FIG. 6B is a bottom view of the hot and cold pack for pregnant women' breast treatment to which the length adjustment unit according to the second embodiment of the present disclosure has been applied.

Referring to FIGS. 6A and 6B, a length adjustment unit 230 according to the second embodiment of the present disclosure may be a Velcro including a hook 231 and a loop 232.

According to the present embodiment, the hook 231 may be provided on one side of the open portion 260 of the cover 210. The loop 232 may be provided in plurality on the other side of the open portion 260 of the cover 210. In a hot and cold pack 200 for pregnant women' breast treatment according to the present embodiment, as the hook 231 is attached to a loop 232 farther from the open portion 260 of the cover 210, the cover 210 may be deformed so that an angle between the cover 210 and the ground increases.

The user may attach the hook 231 to a suitable loop 232 enabling the cover 210 to be suitably deformed into the shape of the user's breast from among the plurality of loops 232 according to the shape of the user's breast, thereby deforming and fixing the hot and cold pack 200 and then using the same.

Figure 7A:
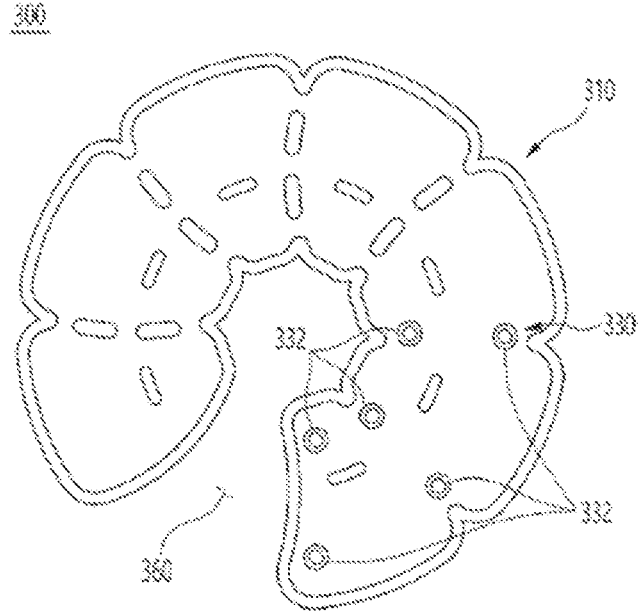
FIG. 7A is a plan view of a hot and cold pack for pregnant women' breast treatment to which a length adjustment unit according to a third embodiment of the present disclosure has been applied.
Figure 7B:
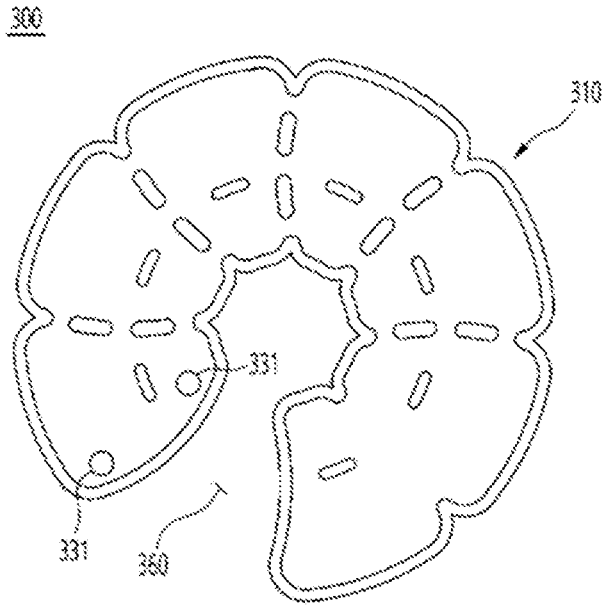
FIG. 7B is a bottom view of the hot and cold pack for pregnant women' breast treatment to which the length adjustment unit according to the third embodiment of the present disclosure has been applied.

FIG. 7A is a plan view of a hot and cold pack for pregnant women' breast treatment to which a length adjustment unit according to a third embodiment of the present disclosure has been applied, and FIG. 7B is a bottom view of the hot and cold pack for pregnant women' breast treatment to which the length adjustment unit according to the third embodiment of the present disclosure has been applied.

Referring to FIGS. 7A and 7B, a length adjustment unit 330 according to the third embodiment of the present disclosure may include an embossed button 331 and an engraved button 332.

According to the present embodiment, the embossed button 331 may be provided on one side of an open portion 360 of a cover 310. The engraved button 332 may be provided on the other side of the open portion 360 of the cover 310 and may be coupled with the embossed button 331. The engraved button 332 may be provided in plurality in a circumferential direction of the cover 310. In a hot and cold pack 300 for pregnant women' breast treatment according to the present embodiment, as the embossed button 331 is coupled with an engraved button 332 farther from the open portion 360 of the cover 310, the cover 310 may be deformed so that an angle between the cover 310 and the ground increases.

The user may couple the embossed button 331 to a suitable engraved button 332 enabling the cover 310 to be suitably deformed into the shape of the user's breast from among the plurality of engraved buttons 332 according to the shape of the user's breast, thereby deforming and fixing the hot and cold pack 300 and then using the same.

Figure 8:
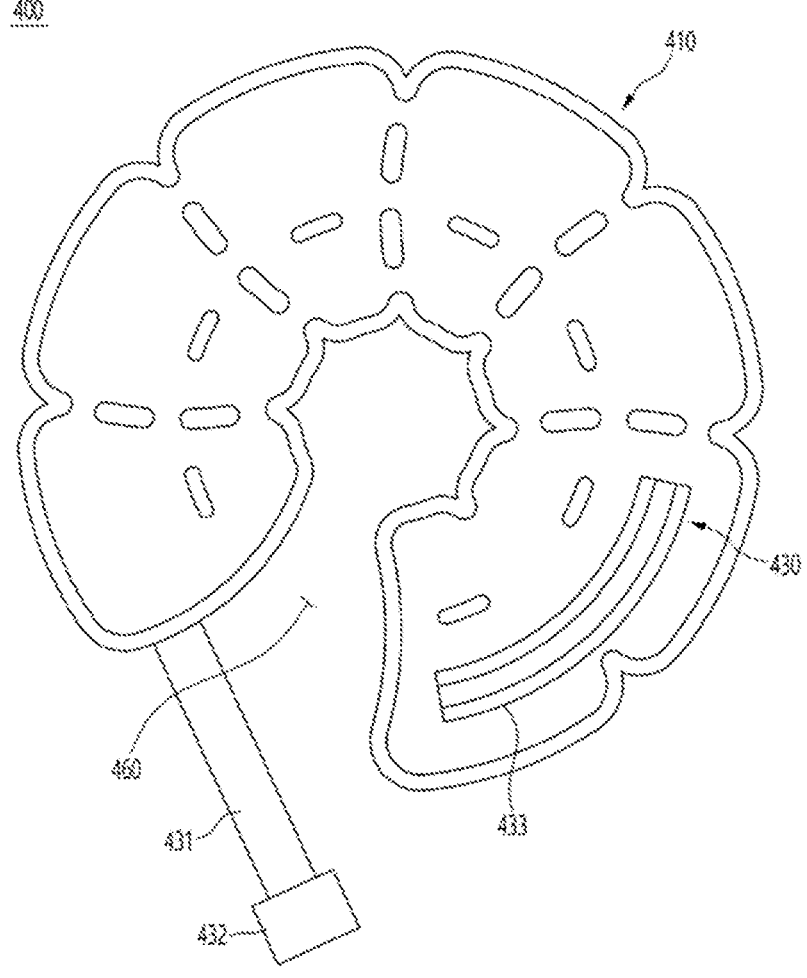
FIG. 8 is a plan view of a hot and cold pack for pregnant women' breast treatment to which a length adjustment unit according to a fourth embodiment of the present disclosure has been applied.

FIG. 8 is a plan view of a hot and cold pack for pregnant women' breast treatment to which a length adjustment unit according to a fourth embodiment of the present disclosure has been applied.

Referring to FIG. 8, a length adjustment unit 430 according to the fourth embodiment of the present disclosure may include a strap 431, a guide portion 432, and a sliding portion 433.

According to the present embodiment, the strap 431 may be provided on one side of an open portion 460 of a cover 410 and may have a predetermined length. The guide portion 432 may be provided on one end of the strap 431. The sliding portion 433 may be provided on the other side of the open portion 460 of the cover 410. The sliding portion 433 may be formed in the form of a rail, and the guide portion 432 may be coupled to the sliding portion 433 to guide a linear movement. When the guide portion 432 moves in a direction away from the open portion 460 of the cover 410 along the sliding portion 433, the strap 431 connected to the guide portion 432 is pulled, and thus one side of the cover 410 connected to the strap 431 may also be pulled. In other words, the farther the guide portion 432 is positioned from the open portion 460 of the cover 410, the cover 410 may be deformed so that an angle between the cover 410 and the ground increases.

The user may use a hot and cold pack 400 for breast treatment for pregnant women by adjusting the guide portion 432 to a location on the sliding portion 433 where the cover 410 is suitably deformed according to the shape of the user's breast.

While the present disclosure has been particularly shown and described with reference to exemplary embodiments thereof, it will be understood by those of ordinary skill in the art that various changes in form and details may be made therein without departing from the spirit and scope as defined by the following claims

The invention claimed is:

1. A hot and cold pack for breast treatment, the hot and cold pack comprising:

a cover including a through hole in a center thereof, the through hole being configured to pass a nipple of a user therethrough, the cover having an annular shape having an open portion to adjust a size of the cover according to a size of a breast of the user while wrapping and covering the breast;

a thermal insulating material filled inside the cover; and a length adjustment unit disposed in the open portion of the cover to connect both sides of the cover at the open portion, the length adjustment unit being configured to adjust the size of the cover, the length adjustment unit including a strap, wherein the cover includes a folding guide unit configured to guide the cover to be curved and folded into a shape corresponding to a shape of the breast, wherein the folding guide unit includes:

a plurality of radial junctions spaced apart from each other along a circumferential direction of the cover at predetermined intervals, each radial junction extending from a circumference of the through hole to an outer circumference of the cover; and a plurality of circumferential junctions spaced apart from each other along a radial direction of the cover at predetermined intervals, each circumferential junction extending from one radial junction portion to another adjacent radial junction, wherein the cover comprises an upper cover and a lower cover each having an annular shape with an open portion, the upper cover and the lower cover being bonded to each other at the plurality of radial junctions and the plurality of circumferential junctions, wherein the plurality of circumferential junctions and the plurality of radial junctions separate an inner space of the cover into a plurality of sealed spaces to prevent movement of the thermal insulating material between the plurality of sealed spaces.

2. The hot and cold pack of claim 1,
wherein the strap of the length adjustment unit is disposed on one side of the open portion of the cover and has a predetermined length,
wherein the length adjustment unit further comprises:
a fastener disposed on an opposite side of the open portion of the cover and including a slit configured to fasten the strap therethrough, and
wherein the strap is configured to be inserted into an insertion hole between the fastener and the cover and then reinserted into the slit to be fixed.

3. The hot and cold pack of claim 1, wherein the length adjustment unit further includes a hook-and-loop fastener including a hook disposed on one side of the open portion of the cover and a loop disposed on an opposite side of the open portion of the cover.

4. The hot and cold pack of claim 1,
wherein the length adjustment unit further includes an embossed button disposed on one side of the open portion of the cover and an engraved button disposed on an opposite side of the open portion of the cover, the engraved button being configured to be coupled with the embossed button, and
wherein the engraved button includes a plurality of engraved buttons along a circumferential direction of the cover, and the size of the cover is configured to be adjusted according to a position of engagement with the embossed button.

5. The hot and cold pack of claim 1,
wherein the length adjustment unit further comprises:
a strap disposed on one side of the open portion of the cover and having a predetermined length;
a guide portion disposed on one end of the strap; and
a sliding portion disposed on an opposite side of the open portion of the cover, the sliding portion being configured to be coupled with the guide portion to guide a linear movement, and
wherein as the guide portion moves on the sliding portion, the size of the cover is configured to be adjusted.

6. The hot and cold pack of claim 1, wherein the through hole is cut at regular intervals in a circumferential direction of the through hole to bend the cover.

7. The hot and cold pack of claim 1, further comprising an outer covering configured to absorb sweat of the user and having a shape corresponding to the annular shape of the cover to surround the cover, wherein the outer covering comprises one or more openings so that the length adjustment unit is usable while the outer covering wraps the cover.

8. The hot and cold pack of claim 1, further comprising a nipple protection unit fitted along a circumference of the through hole to protect the nipple of the user, the nipple protection unit having a circumferential body corresponding to the circumference of the through hole.

* * * * *